US00PP31415P3

(12) United States Plant Patent
Suphachadiwong

(10) Patent No.: US PP31,415 P3
(45) Date of Patent: Jan. 28, 2020

(54) *VANDA* PLANT NAMED 'SPCDEW1712'

(50) Latin Name: *Vanda* spp. Jones ex R. Br.
Varietal Denomination: SPCDW1712

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 16/350,785

(22) Filed: Jan. 14, 2019

(65) Prior Publication Data

US 2019/0223357 P1 Jul. 18, 2019

(30) Foreign Application Priority Data

Jan. 16, 2018 (QZ) ..... PBR 2018/0179

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02; A01H 6/62
See application file for complete search history.

*Primary Examiner* — Annette H Para
(74) *Attorney, Agent, or Firm* — Samuel R. McCoy, Jr.

(57) ABSTRACT

A new and distinct *Vanda* plant named 'SPCDW1712' which is characterized by a compact growth habit with improved plant vigor and a freely flowering bloom habit, an abundance of large flowers, proportionately arranged on an inflorescence which is carried well above the foliage, white flowers with dark violet, conspicuous reticulate veining, exhibits a labellum with a very dark violet central lobe, and light violet lateral lobes, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1712'.

CROSS REFERENCE TO RELATED APPLICATIONS

This application claims priority to the Community Plant Variety Rights application number 2018/0179, filed Jan. 16, 2018, which is herein incorporated by reference.

BACKGROUND OF THE INVENTION

Parentage: The new *Vanda* plant, 'SPCDW1712', is the result of a planned breeding program. 'SPCDW1712' originated as a seedling from the controlled pollination of *Vanda* 'S76' (not patented), the seed parent, with *Vanda* 'A274' (not patented), the pollen parent. Both parents were developed by, and are owned by, the inventor and were never commercially released. The crossing was made by the inventor in his research greenhouse in Bangphra, Thailand in April of 1994.

The new variety was first selected in September of 1998, in a research greenhouse in Bangphra, Thailand belonging to the inventor. After identifying the new variety as a potentially interesting selection, the inventor continued confidential testing and propagation of 'SPCDW1712', assessing stability of the unique characteristics of this variety.

Asexual Reproduction: Asexual September of 2011 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1712' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1712'. These characteristics in combination distinguish 'SPCDW1712' as a new and distinct *Vanda* cultivar:

1. *Vanda* 'SPCDW1712' exhibits a compact growth habit, with improved plant vigor and a freely flowering bloom habit; and
2. *Vanda* 'SPCDW1712' exhibits an abundance of large flowers, proportionately arranged on an inflorescence which is carried well above the foliage; and
3. *Vanda* 'SPCDW1712' exhibits white flowers with dark violet, conspicuous reticulate veining; and
4. *Vanda* 'SPCDW1712' exhibits a labellum with a very dark violet central lobe, and light violet lateral lobes.

BOTANICAL DESCRIPTION OF THE PLANT

Figure 1:
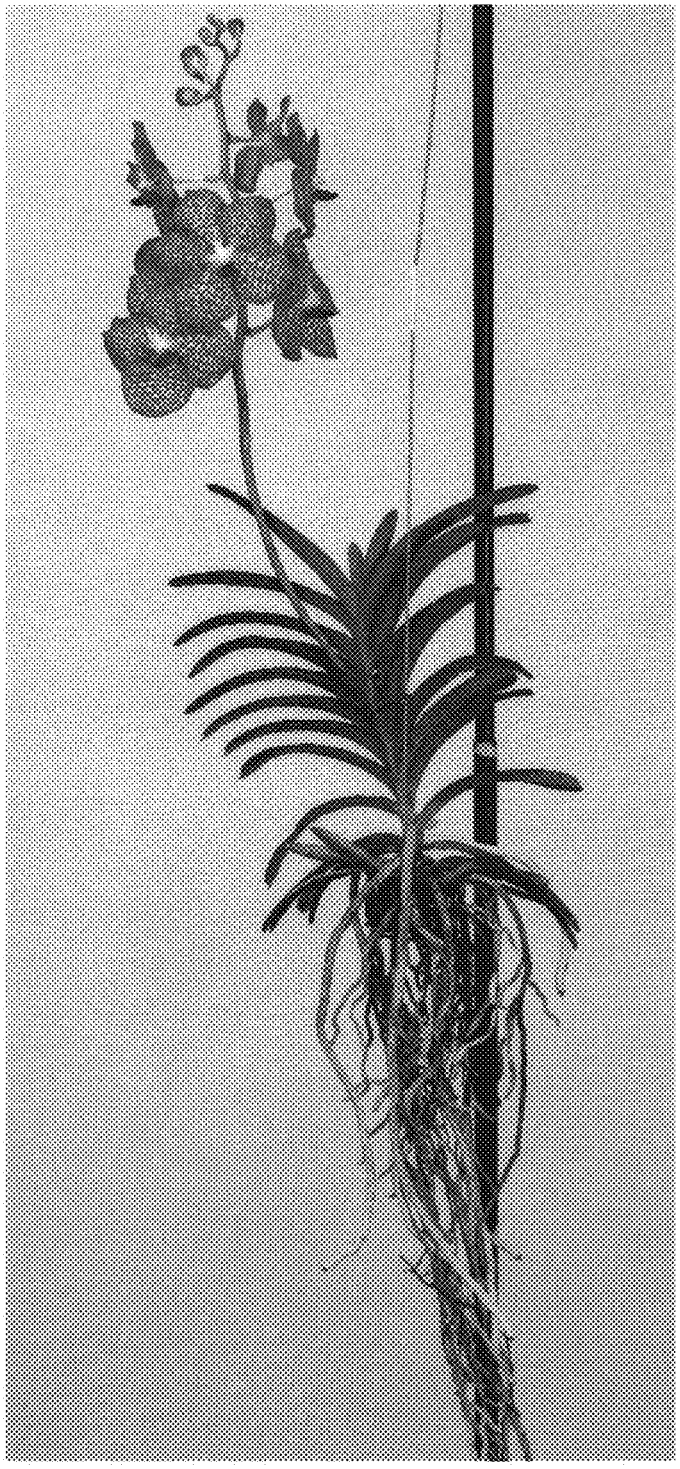
FIG. 1 illustrates, as nearly true as it is reasonably possible to make the same in color photographs of this type, an exemplary plant of 'SPCDW1712' grown in a commercial greenhouse in Honselersdijk, the Netherlands. This plant is approximately 6 years old from the time of mericloning, shown planted in an 8 by 2 cm container.
Figure 2:
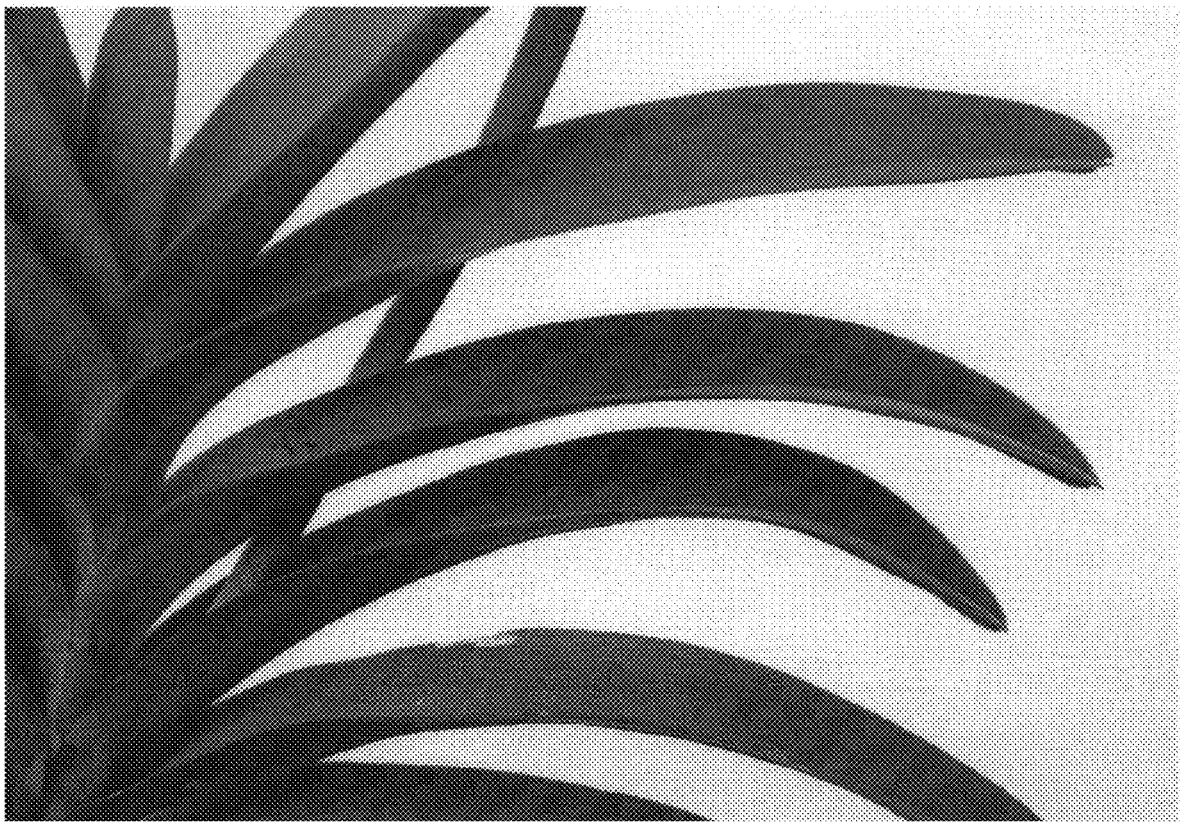
FIG. 2 illustrates, as nearly true as it is reasonably possible to make the same in color photographs of this type, the typical foliage of 'SPCDW1712'.
Figure 3:
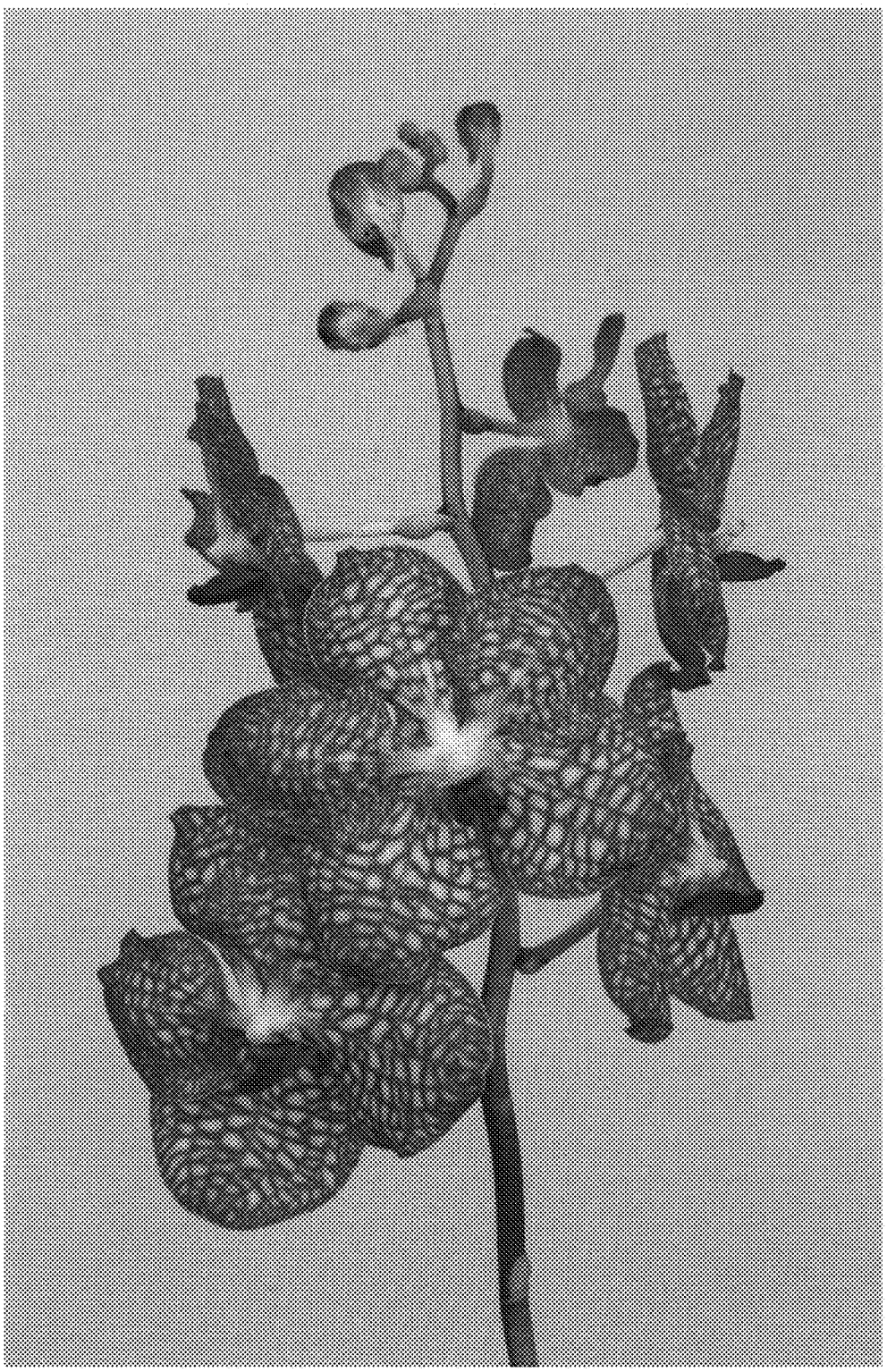
FIG. 3 illustrates, as nearly true as it is reasonably possible to make the same in color photographs of this type, the typical inflorescence of 'SPCDW1712'.
Figure 4:
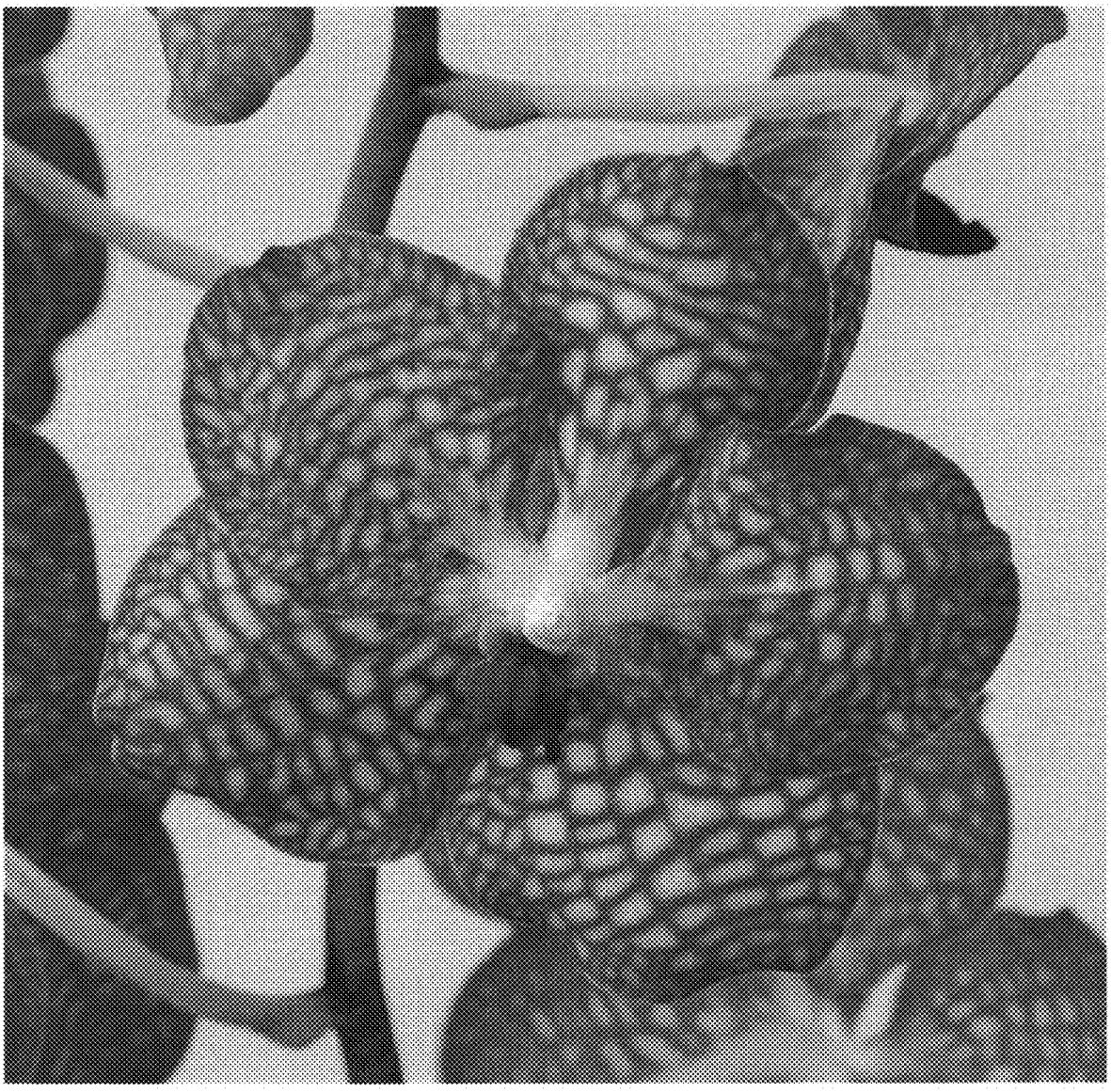
FIG. 4 illustrates, as nearly true as it is reasonably possible to make the same in color photographs of this type, the typical flower of 'SPCDW1712'.

The following observations and measurements made in August of 2018 describe averages from a sample set of six specimens of six year-old 'SPCDW1712' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1712' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1712' and comparisons with the parents and most similar commercial variety of *Vanda* are provided below.

Plant description:

- *Growth habit.*—Perennial; monopodial, upright. Single monopodial leafy stem, with flowers carried well above the leaf plane; inflorescences growing from the leaf axils.
- *Average height from base (plant grown in hanging basket, so no soil line present) to foliar plane.*—31.8 cm.
- *Average height from base (plant grown in hanging basket, so no soil line present) to top of floral plane.*—68.9 cm.
- *Plant spread.*—Average of 33.0 cm.
- *Appropriate container size.*—8 cm by 2 cm rectangular hanging basket.
- *Growth rate.*—Moderate.
- *Plant vigor.*—Moderate.
- *Propagation type.*—Meristematic tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Plants have not been observed to be susceptible or resistant to pathogens and pests common to *Vanda*.
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Moderately to densely rooting; with aerial roots only.
- *Dimensions, mature roots.*—53.5 cm long with a diameter of 0.5 cm, on average.
- *Texture.*—Very fleshy; non-fibrous.
- *Color.*—Greyed-green, nearest to in between RHS 192C and 192D; root apex is yellow-green, RHS 146B.

Stem:

- *Branching habit.*—Monopodial; no lateral branches present.
- *Number of primary (main) stems per plant.*—One.
- *Number of secondary (lateral) branches per plant.*—None.
- *Aspect.*—Circular, formed by the leaf sheaths.
- *Length.*—19.4 cm.
- *Diameter.*—0.8 cm.
- *Internode length.*—0.8 cm.
- *Luster.*—Matte.
- *Attitude, main stem.*—Near vertical.
- *Strength.*—Very strong.
- *Color, juvenile.*—Yellow-green, nearest to RHS 145C.
- *Color, mature.*—Yellow-green, nearest to RHS 145C.
- *Color at internodes.*—Yellow-green, nearest to RHS 145C, and moderately to heavily suffused with greyed-yellow, nearest to RHS 162C.
- *Pubescence.*—Glabrous.

Foliage:

- *Arrangement.*—Distichous.
- *Dimensions.*—16.4 cm long, excluding the sheath, and 2.7 cm wide.
- *Shape of blade.*—Ligulate.
- *Aspect.*—Moderately to strongly carinate and slightly to moderately curled downward.
- *Apex.*—Unequal praemorse.
- *Base.*—Sheathing.
- *Sheath dimensions.*—3.6 cm long and 1.1 cm wide, on average.
- *Sheath color.*—Yellow-green, nearest to RHS 145C.
- *Margin.*—Entire.
- *Pubescence, texture and luster of adaxial surface.*—Glabrous, smooth, and matte.
- *Pubescence, texture and luster of abaxial surface.*—Glabrous, smooth, and matte.
- *Color.*—Juvenile foliage, adaxial surface — Yellow-green, nearest to RHS 144A, and becoming green towards the margins and apex, nearest to in between RHS 143A and 143B. Juvenile foliage, abaxial surface — Yellow-green, nearest to in between RHS 144A and 146B; darker towards the apex, nearest to in between RHS 144A and 146B. Mature foliage, adaxial surface — Nearest to in between green and yellow-green, RHS 137B and 146B; margined green, nearest to RHS NN137B. Mature foliage, abaxial surface — Yellow-green, nearest to RHS 146B; margined green, nearest to RHS 137A.

*Venation.*—Pattern — Parallel. Color, adaxial surface — Yellow-green, nearest to RHS 144A. Color, abaxial surface — Yellow-green, nearest to in between RHS 144B and 144C.

*Petiole.*—No petioles present; leaves sessile.

Inflorescence:

*Inflorescence arrangement.*—Axially placed raceme.

*Natural flowering season.*—Autumn into winter.

*Time to flower.*—Approximately 10 months.

*Flowers per inflorescence.*—Average of 14.

*Flowers per plant.*—8 open flowers and 6 flower buds.

*Inflorescence height.*—Approximately 36.3 cm (measured from base of lowest flower to top of upper flower).

*Inflorescence diameter.*—Approximately 17.7 cm.

*Peduncle.*—Dimensions — Approximately 59.5 cm long and 0.8 cm wide. Attitude — Generally at a 30 degree angle to lateral branch axis. Strength — Moderately strong. Texture and luster — Glabrous and matte. Color — Yellow-green, nearest to RHS 144A.

Bud:

*Length.*—Average of 2.2 cm.

*Diameter.*—Average horizontal diameter is 1.7 cm; the vertical diameter is 2.5 cm.

*Shape.*—Cubic, with a deltoid apex which is pointed downward.

*Pubescence, texture and luster.*—Glabrous, smooth and matte.

*Color, upper surface.*—Yellow-green, nearest to in between RHS 145B and 145C, and suffused with purple, nearest to RHS N77D.

*Color, lower surface.*—Violet, nearest to RHS 86B, and fading lighter towards the base, nearest to a mixture of RHS 85A and 86D; base is yellow-green, nearest to RHS 145C.

Flower:

*Flower type.*—Zygomorphic (orchidaceous), typical shape for the genus *Vanda*.

*Flowering habit.*—Moderately free flowering.

*Shape.*—Zygomorphic, single; consisting of three sepals and three petals, one of which is transformed into a labellum; the two lateral petals moderately overlap the lateral sepals and slightly to moderately overlap the dorsal sepal; lateral sepals are touching to slightly overlapping one another.

*Attitude.*—Flowers are outward-facing to slightly nodding.

*Vertical height.*—Approximately 11.0 cm.

*Diameter.*—Approximately 10.6 cm.

*Depth.*—Approximately 3.7 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 5.4 cm. Width — Approximately 4.8 cm. Shape — Broad ovate. Apex — Obtuse. Base — Cuneate. Margin — Entire; moderately to highly undulated. Pubescence, texture and luster of upper surface — Glabrous, velvety and matte. Pubescence, texture and luster of lower surface — Glabrous, velvety and matte. Color when opening, upper surface — White, nearest to RHS NN155B, and becoming heavily suffused with violet towards the margins and apex, nearest to RHS N88C; conspicuous reticulate veining colored violet, nearest to RHS N88B; the base of the petals are finely dotted with violet, nearest to RHS N88A. Color when opening, lower surface — Violet, nearest to RHS N88D; darker towards the margins and apex, nearest to RHS N88C; conspicuous reticulate veining colored violet, nearest to RHS N88B. Color when fully opened, upper surface — White, nearest to a mixture of RHS NN155B and NN155C, and very lightly suffused with violet, nearest to RHS N88B, and becoming heavily suffused with violet towards the margins and apex, nearest to a mixture of RHS N88C and N88D. Color when fully opened, lower surface — Violet, nearest to in between RHS 85A and N88D; darker towards the margins and apex, nearest to in between RHS N88C and N88D. Fading, upper surface — Not fading. Fading, lower surface — Not fading. Venation — Very conspicuous, dense reticulate veining. Venation color, fully opened, upper surface — Violet, nearest to RHS N88B, and darker towards the distal margins and apex, nearest to RHS N88A. Venation color, fully opened, lower surface — Violet, nearest to RHS N88B, and darker towards the distal margins and apex, nearest to RHS N88A.

*Labellum.*—Shape — Three-lobed; the lateral lobes are obovate, and strongly involute; the central lobe is oblong, and strongly revolute. Length — Central lobe — Approximately 2.5 cm. Lateral lobes — Approximately 0.4 cm. Width — Central lobe — Approximately 1.3 cm at the base; 1.1 at the apex. Lateral lobes — Approximately 0.7 cm. Apex — Central lobe — Emarginate. Lateral lobes — Emarginate. Base — Central lobe — Broad cuneate. Lateral lobes — Broad cuneate. Margin — Central lobe — Entire; very slightly undulated. Lateral lobes — Entire; not undulated. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — Violet, nearest to in between RHS N87A and N88A. Lateral lobes — Violet, nearest to RHS 84C, and radially striped with a darker shade of violet, nearest to RHS 84A; fading to purple-violet at the base, nearest to RHS N82A, with a yellow-orange dot at the point of attachment near the column, nearest to in between RHS 17A and 17B. Color when opening, lower surface — Central lobe — Violet, nearest to RHS N88A, and fading to a lighter shade of violet towards the base, nearest to in between RHS N88C and N88D. Lateral lobes — Violet, nearest to RHS 85C. Color when fully opened, upper surface — Central lobe — Violet, nearest to RHS N88A, and fading slightly to a lighter shade of violet at the base, nearest to RHS N88B. Lateral lobes — Violet, nearest to RHS 85A, and becoming a dark purple-violet towards the base, nearest to RHS N82A; heavily suffused with yellow-orange at the point of attachment near the column, nearest to RHS 17B. Color when fully opened, lower surface — Central lobe — Violet, nearest to RHS N88A, and fading to a lighter shade of violet towards the base, nearest to RHS N88C. Lateral lobes — Violet, nearest to RHS 85A. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities.*—Dimensions — 1.8 cm long and 1.0 cm wide, on average. Color — Violet, nearest to RHS N88A, and fading to a lighter shade of violet towards the base, nearest to RHS 85C.

*Spurs.*—Quantity — Average of 1. Length — Approximately 1.1 cm. Diameter — Approximately 0.3 cm. Vertical height — Approximately 0.6 cm, at the base. Shape — Short triangular; flattened. Apex — Bluntly acute. Base — Broad cuneate. Pubescence, texture and luster — Glabrous, smooth, and matte. Color — Violet, nearest to RHS 85D, and radially striped with a darker shade of violet, nearest to RHS 85B.

*Sepals.*—Quantity — Average of 3 unfused sepals. Arrangement — One dorsal sepal and two lateral sepals. Length — Dorsal sepal — Approximately 5.5 cm. Lateral sepals — Approximately 5.8 cm. Width Dorsal sepal — Approximately 4.5 cm. Lateral sepals — Approximately 5.9 cm. Shape — Dorsal sepal — Broad ovate to broad oblong. Lateral sepals — Near orbicular. Apex — Dorsal sepal — Rounded. Lateral sepals — Rounded. Base — Dorsal sepal — Cuneate. Lateral sepals — Cuneate. Margin — Dorsal sepal — Entire; lightly coarsely undulated. Lateral sepals — Entire; lightly coarsely undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — White, nearest to a mixture of RHS NN155C and NN155D, heavily suffused with violet towards the margins and apex, nearest to RHS N88C, and darker violet towards the top of the sepal, nearest RHS N88A; conspicuous reticulate veining colored violet, nearest to RHS N88B. Lateral sepals — White, nearest to a mixture of RHS NN155C and NN155D, heavily suffused with violet towards the margins and apex, nearest to RHS N88C, and darker violet towards the top of the sepal, nearest RHS N88A; conspicuous reticulate veining colored violet, nearest to RHS N88B. Color when opening, lower surface — Dorsal sepal — Violet, nearest to in between RHS 85A and N88D; darker towards the margins and apex, nearest to RHS N88C; conspicuous reticulate veining colored violet, nearest to RHS N88B. Lateral sepals — Violet, nearest to in between RHS 85A and N88D; darker towards the margins and apex, nearest to RHS N88C; cons Color when fully opened, upper surface — Dorsal sepal — White, nearest to a mixture of RHS NN155C and NN155D, and very lightly suffused with violet, nearest to RHS 85D, and becoming heavily suffused with violet towards the margins and apex, nearest to RHS N88D. Lateral sepals — White, nearest to a mixture of RHS NN155C and NN155D, and very lightly suffused with violet, nearest to RHS 85D, and becoming heavily suffused with violet towards the margins and apex, nearest to RHS N88D. Color when fully opened, lower surface — Dorsal sepal — Violet, nearest to RHS 85D; darker towards the margins and apex, nearest to RHS N88C. Lateral sepals — Violet, nearest to RHS 85D; darker towards the margins and apex, nearest to RHS N88C. Fading, upper surface — Not fading. Fading, lower surface — Not fading. Venation — Densely reticulate. Venation color, fully opened, upper surface — Dorsal sepal — Violet, nearest to a mixture of RHS N88A and N88B, and darker towards the distal margins and apex, nearest to RHS N88A. Lateral sepals — Violet, nearest to a mixture of RHS N88A and N88B, and darker towards the distal margins and apex, nearest to RHS N88A. Venation color, fully opened, lower surface — Dorsal sepal — Violet, nearest to a mixture of RHS N88A and N88B, and darker towards the distal margins and apex, nearest to RHS N88A. Lateral sepals — Violet, nearest to a mixture of RHS N88A and N88B, and darker towards the distal margins and apex, nearest to RHS N88A.

*Pedicels.*—Length — Approximately 6.9 cm. Diameter — Approximately 0.5 cm. Attitude — Approximately 80 degree angle to peduncle axis. Strength — Moderate. Texture — Glabrous, axially angled with 5 "ribs", axially twisted (due to resupination). Luster — Moderately glossy. Color — Violet, nearest to RHS 84D, and fading to purple towards the distal end, nearest to RHS 76D.

*Bract.*—Quantity — One bract present at the base of each pedicel. Shape — Broad oblong to broad obovate; folded around the base of each pedicel. Dimensions — Average of 1.4 cm long and 1.3 cm wide. Apex — Broad obtuse. Base — Broad cuneate. Margins — Entire. Color, inner surface — Yellow-green, nearest to a mixture of RHS N144A and N144B. Color, outer surface — Yellow-green, nearest to a mixture of RHS N144A and N144B.

Reproductive organs:

*Column.*—Length — Approximately 0.6 cm. Diameter — Approximately 0.7 cm. Color — White, nearest to RHS NN155C; base is suffused with purple on the upper surface, nearest to RHS 76D.

*Ovary.*—Position — Inferior. Diameter — Approximately 0.2 cm. Color — Yellow-green, nearest to RHS 150D.

*Pollinia color.*—Yellow-orange, nearest to RHS 15A.

Seed and fruit: No fruit and seed production has been detected to date.

COMPARISON WITH THE PARENT PLANTS

Plants of the new cultivar 'SPCDW1712' differ from the *Vanda* seed parent, 'S76' (not patented), by the characteristics described in Table 1.

TABLE 1

| Characteristic | 'SPCDW1712' | 'S76' |
|---|---|---|
| Vigor; rate of growth. | Easier to propagate and faster growing that 'S76'. | More difficult to propagate and slower growing than 'SPCDW1712'. |
| Root system. | More densely rooted. | Less densely rooted. |
| Bloom habit. | More freely flowering. | Less freely flowering. |
| Arrangement of flowers on the inflorescence. | Proportionately arranged around the peduncle. | Disproportionately arranged on the peduncle. |
| Quantity of flowers per inflorescence. | More flowers than 'S76'. | Fewer flowers than 'SPCDW1712'. |
| Flower size. | Larger than 'S76'. | Smaller than 'SPCDW1712'. |

Plants of the new cultivar 'SPCDW1712' differ from the *Vanda* pollen parent, *Vanda* 'A274' (not patented), by the characteristics described in Table 2.

TABLE 2

| Characteristic | 'SPCDW1712' | 'A274' |
|---|---|---|
| Growth habit. | More compact than 'A274'. | Less compact than 'SPCDW1712'. |
| Bloom habit. | More freely flowering. | Less freely flowering. |
| Inflorescence height. | Taller than 'A274'. | Shorter than 'SPCDW1712'. |
| Arrangement of flowers in the inflorescence. | Proportionately arranged around the peduncle. | Disproportionately arranged on the peduncle. |
| Overlaid color pattern of the petals and sepals. | Conspicuously reticulate. | More spotted than reticulated. |

COMPARISON WITH THE MOST SIMILAR *VANDA* CULTIVAR KNOWN TO THE INVENTOR

Plants of the new cultivar 'SPCDW1712' are similar to the cultivar, *Vanda* 'SPCDW1102' (Netherlands Plant Breeder's Rights grant number 20716). A comparison of 'SPCDW1712' with *Vanda* 'Magic Blue' is described in Table 3.

TABLE 3

| Characteristic | 'SPCDW1712' | 'Magic Blue' |
|---|---|---|
| Foliage length. | Shorter than 'Magic Blue'. | Longer than 'SPCDW1712'. |
| Foliage color. | Darker green. | Lighter green. |
| Aspect of the flower petals and sepals. | Not axially twisted. | Heavily axially twisted; spiralled. |
| Margin undulation of the flower petals and sepals. | Less undulated. | More heavily undulated. |
| General coloration of the petals and sepals when fully opened, excluding the reticulation. | White and very lightly suffused with violet. | White and moderately suffused with violet. |
| Prominence of reticulation. | More prominent. | Less prominent. |
| Color of the reticulation. | Darker violet. | Lighter violet. |
| Width of the central lobe of the labellum. | Wider than 'Magic Blue'. | Narrower than 'SPCDW1712'. |

That which is claimed is:

1. A new and distinct variety of *Vanda* plant named 'SPCDW1712', substantially as described and illustrated herein.

* * * * *